United States Patent [19]

Cavanak

[11] 4,388,307

[45] Jun. 14, 1983

[54] GALENICAL COMPOSITIONS

[75] Inventor: Thomas Cavanak, Oberwil, Switzerland

[73] Assignee: Sandoz Ltd., Basel, Switzerland

[21] Appl. No.: 347,276

[22] Filed: Feb. 9, 1982

Related U.S. Application Data

[63] Continuation-in-part of Ser. No. 208,181, Nov. 19, 1980, abandoned, which is a continuation-in-part of Ser. No. 82,487, Oct. 9, 1979, abandoned, which is a continuation of Ser. No. 16,950, Mar. 2, 1979, abandoned.

[30] Foreign Application Priority Data

Mar. 7, 1978 [CH] Switzerland ............... 2461/78
Mar. 14, 1978 [CH] Switzerland ............... 8634/78

[51] Int. Cl.³ .................. A61K 37/00; A61K 47/00
[52] U.S. Cl. ........................... 424/177; 424/365
[58] Field of Search .................. 424/177, 365

[56] References Cited

U.S. PATENT DOCUMENTS

| 3,288,824 | 11/1966 | Mahier et al. | 424/365 |
| 3,881,012 | 4/1975 | Mima et al. | 424/365 |
| 4,073,920 | 2/1978 | Dowrick | 424/365 |
| 4,108,985 | 8/1978 | Rüegger et al. | 424/177 |

FOREIGN PATENT DOCUMENTS

| 2253531 | 12/1974 | France | 424/177 |
| 2330387 | 11/1976 | France | 424/177 |
| 2390420 | 5/1978 | France | 424/177 |

Primary Examiner—Delbert R. Phillips
Attorney, Agent, or Firm—Gerald D. Sharkin; Robert S. Honor; Walter F. Jewell

[57] ABSTRACT

The present invention provides a pharmaceutical composition comprising a pharmacologically active monocyclic peptide and a carrier comprising at least one of the following components:
(a) a non-ionic ester of a triglyceride and a polyalkylene polyol,
(b) a saturated fatty acid triglyceride, and
(c) a mono- or di-glyceride
having improved physical and absorption properties.

15 Claims, No Drawings

GALENICAL COMPOSITIONS

This is a continuation-in-part of our co-pending application Ser. No. 208,181, filed Nov. 19th, 1980, now abandoned which in turn in a continuation-in-part of our application Ser. No. 82,487, filed Oct. 9th, 1979, now abandoned, which in turn was a continuation of our application Ser. No. 16,950, filed Mar. 2nd, 1979, now abandoned.

This invention relates to galenical compositions, particularly compositions containing a pharmacologically active mono-cyclic peptide.

Because of the hydrophobic and/or lipophilic character of such peptides, pharmaceutical formulations thereof with conventional solid or liquid pharmaceutical excipients tend to have disadvantages. For example the peptide may not be satisfactorily absorbed, the composition may not be well tolerated, the composition may not be sufficiently stable on storage, e.g. against crystallizing-out of the peptide, and/or the concentration of the peptide capable of being solubilized without crystallizing-out may be low, e.g. of the order of 3% or lower.

Problems of this nature arise not only with liquid formulations, but such solid forms such as solid "solutions", e.g. in the form of oral pellets, produced for example by melting a solid carrier, mixing in the active ingredients and allowing the mixture to solidify.

While there are many known proposals to alleviate or overcome problems of this type, it has been found after exhaustive trials that many of these proposals are inadequate in the area of the monocyclic peptides, in particular cyclosporins, with which the invention is concerned. It has, however, surprisingly been found that certain classes of glycerides used as carrier components do assist in alleviating these difficulties; in particular they, for example, may enable achievement of higher blood levels of active agent or avoid other problems such as instability.

The present invention accordingly provides a pharmaceutical composition comprising a pharmacologically active mono-cyclic peptide and carrier comprising at least one of the following components:

(a) a trans esterification product of a natural or hydrogenated vegetable oil triglyceride and a polyalkylene polyol,
(b) a saturated fatty acid triglyceride, and
(c) a mono- or di-glyceride.

The compositions of the invention are particularly suitable for hydrophobic and/or lipophilic peptides which are insoluble or difficultly soluble in conventional pharmaceutical vehicles, in particular cyclosporins, including those having a basic ring structure as follows:

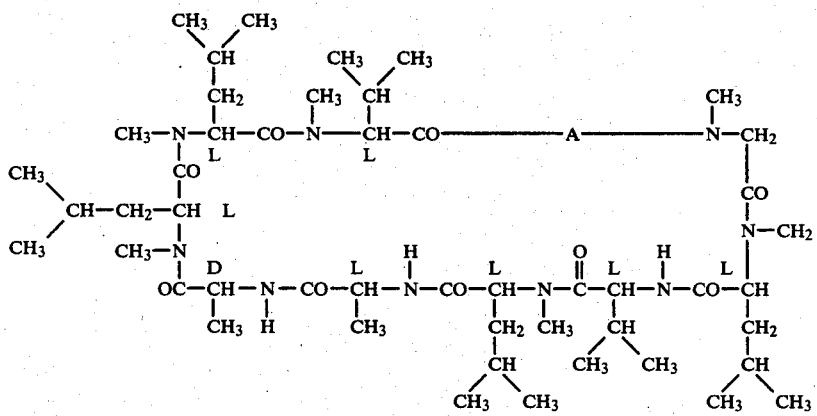

wherein A is a bivalent moiety containing two amino acids linked together.

A may be for example:

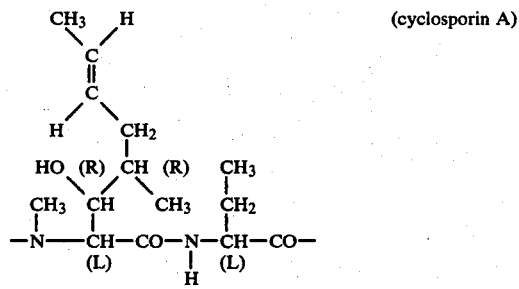     (cyclosporin A)

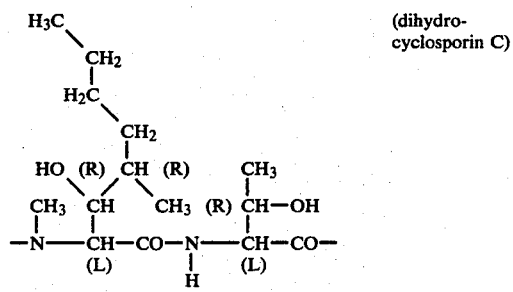     (dihydro-cyclosporin C)

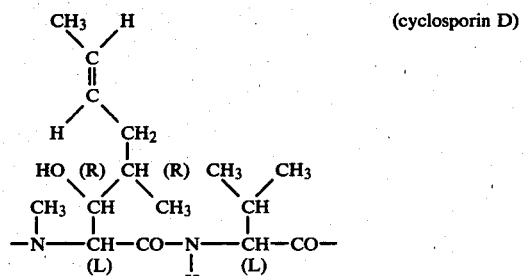     (cyclosporin D)

-continued

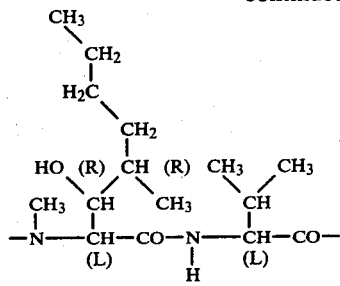
(dihydrocyclosporin D), or

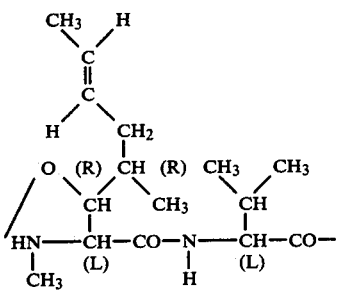
(iso-cyclosporin D)

Cyclosporin A, dihydrocyclosporin C and isocyclosporin D are the preferred peptides. Cyclosporins e.g. as identified above are known compounds having known pharmacological activity, e.g. as described in U.S. Pat. Nos. 4,117,118 and 4,108,985 and in Belgian Pat. No. 866,810.

Component (a) may be prepared in conventional manner, e.g. as described in U.S. Pat. No. 3,288,824. The ester may be formed by transesterification of a triglyceride particularly a triglyceride from a vegetable oil, e.g. from kernel oil, almond oil, ground nut oil, olive oil and/or palm oil, with one molar part of a polyethylene glycol MW 200 to 800 and obtainable according to the process described in the U.S. Pat. No. 3,288,824 mentioned before, the contents of which are incorporated by reference. These esters may be obtained from Etablissement Gattefosse, Boulogne sur Seine, France, under the trade name LABRAFIL (see Fiedler, Lexikon der Hilfstoffe p. 320, 1971). The preferred ester is Labrafil M 1944 CS (a polyoxyethylated kernel oil) mixture having a density $D^{20}=0.940–0.965$, an acid number <2, an iodine number=60–90, a saponification number=145–175 and a hydrophilic-lipophilic balance (H.L.B.)=4).

Component (b) may be obtained in conventional manner by esterifying a triglyceride with saturated fatty acids having a carbon chain length of 8 to 12 carbons. Generally these glycerides will have an iodine number of less than 2. Examples of the triglycerides with which this invention is concerned are the MIGLYOLS® (Dynamit Nobel Witten/Rukr Germany), especially Miglyol 812, or Myritol 318 (Henkel Düsseldorf, Germany). The physical and chemical composition of Miglyols are shown in Table I.

TABLE I

| | MIGLYOL 810 | MIGLYOL 812 | MIGLYOL 818 | MIGLYOL 840 |
|---|---|---|---|---|
| PHYSICAL CHARACTERISTICS | | | | |
| Acid value | 0.1 max | 0.1 max. | 0.2 max. | 0.1 max. |
| Saponification value | 340–360 | 325–345 | 315–320 | 320–340 |
| Iodine value | 1 max. | 1 max. | 10 max. | 1 max. |
| Unsaponifiable matter (%) | 0.3 max. | 0.3 max. | 0.2 max. | 0.3 max. |
| Iodine colour value | 2.0 max. | 2.0 max. | 3.1 max. | 2.0 max. |
| Cloud point | 0° C. max. | 10° C. max. | 10° C. max. | −10° C. max. |
| Moisture (%) | 0.15 max. | 0.15 max. | 0.15 max. | 0.15 max. |
| Density at 20° C. | 0.94–0.96 | 0.94–0.96 | 0.93–0.95 | 0.92–0.94 |
| Refraction at 20° C. | 1.4490–1.4510 | 1.4480–1.4500 | 1.4490–1.4510 | 1.440–1.442 |
| Viscosity at 20° C. (cps.) | 27–30 | 28–32 | 30–33 | 9–12 |
| DISTRIBUTION OF THE FATTY ACIDS IN THE GLYCERIDE | | | | |
| Fatty Acids | | | | |
| Hexanoic acid ($C_6$) | 2% max. | 3% max. | 3% max. | 3% max. |
| Octanoic acid ($C_8$) | 65–75% | 50–65% | 45–60% | 65–80% |
| Decanoic acid ($C_{10}$) | 25–35% | 30–45% | 25–40% | 15–30% |
| Lauric acid ($C_{12}$) | 2% max. | 5% max. | 2–5% | 3% max. |
| Linoleic acid ($C_{18}$) | — | — | 3–6% | — |

Component (c) is preferably one of the mono- or di-glycerides approved for pharmaceutical use, e.g. a mono- or di-($C_{16}$–$C_{20}$) fatty acid glyceride, e.g. of stearic acid or especially of oleic acid. Preferably component (c) is glycerol mono-oleate (Monooleinum-Pharmacopoea Helvetica Sixth Edition).

Naturally when the components (a) and/or (c) present are solid, these should be chosen such that they can be melted at temperature at which the peptide is stable. Such components include, for example, glycerol monostearate or glycerol di-stearate, and Labrafil 2130.

The preferred total concentration of component (a) and/or component (b) and/or component (c) present in the pharmaceutical compositions according to the invention, as well as the weight ratio of individual components when two or more of these are present, will naturally depend, inter alia, on the particular component(s) used, and in particular on the solvent/solubilizing effect thereof, the particular mono-cyclic peptide used, the concentration of mono-cyclic peptide desired in the final composition and the solvent/solubilizing effect of any further pharmaceutical excipients present. In general the preferred weight ratio of component (a), (b) and/or (c) to peptide is 10 parts in total of the component (or components) to 0.2 to 10 parts of peptide, or more preferably 1 to 10 parts by weight of peptide, and conveniently from 1 to 7 parts by weight of peptide.

The pharmaceutical compositions of the invention may be made by mixing a pharmacologically active mono-cyclic peptide with the liquid carrier comprising component (a) and/or (b) and/or (c) as defined above. If the component (a) or (c) is solid, temperatures up to about 70° C. may be used, to produce a liquid melt in which the active agent may be dissolved in. The composition may be cooled and then, for example, ground.

The pharmaceutical compositions may be formulated in conventional manner, if desired with further pharmaceutical excipients, into forms suitable for oral or parenteral administration. Preferably they are in liquid form.

Examples of preferred compositions are:
(a) Solutions for drinking, e.g. Example 1 hereinafter,
(b) Emulsions for drinking,
(c) Injection solutions, e.g. Examples 2 and 4 hereinafter,
(d) Solutions contained in capsules, e.g. Example 6 hereinafter,
(e) Pellets for oral administration.

The modes of administration are preferably intramuscular and subcutaneous administration or more preferably oral administration. In particular when component (b) is present, the pharmaceutical composition is preferably used for parenteral administration.

The pharmaceutical compositions according to the invention may be formulated with or without further exipients.

In particular solubilizing agents and solvents may be present in a concentration of up to 60% of the total composition, if desired, in order to attain a satisfactory concentration of peptide.

(i) Ethanol may be used as a further solubilizing agent/solvent. The ethanol content by weight may be for example 2 to 5% for parenteral compositions and 1 to 20% for oral compositions, calculated on the total composition.

(ii) For a parenteral composition, an alternative further solubilizing agent/solvent is a benzoic acid benzyl ester. This may be present at from 5 to 40% of by weight of the total composition.

(iii) A vegetable oil, such as olive oil or corn oil, may be present in both oral and parenteral compositions as Vehicle. The vegetable oil content by weight may be for example for 35 to 60%, calculated on the total composition.

(iv) For emulsions for drinking, preferably agent (a) and/or (c) as defined above is present as well as a lecithin such as soya lecithin. Such emulsions may contain from 20% to 80% by weight water and contain ethanol as a solubilizing agent/solvent.

(v) For oral pellets, it is preferred to use a solid or semi-solid component (a) or (c), especially component (c). Colloidal silicic acid, sugar, and microcrystalline cellulose are suitable excipients.

Compositions in accordance with the invention comprising a cyclosporin and a carrier comprising a component (a) together with (i) ethanol and (iii) a vegetable oil as set forth above are especially advantageous in that they provide solutions characterised by a high degree of stability. In particular they exhibit markedly improved stability compared with equivalent compositions in which one or other of the components (i) or (iii) are omitted, particularly when higher concentrations of cyclosporin (e.g. of the order of 10% and even up to 20% by weight based on the total weight of the composition) are present. Thus on storage over longer periods of time, compositions formulated with a carrier comprising (a) and (i) only exhibit cyclosporin precipitation at lower temperatures, e.g. at temperatures of ca. 5° C., such as are commonly employed for storage of pharmaceuticals, e.g. in hospitals, while compositions formulated with a carrier comprising (a) and (iii) only, exhibit cyclosporin precipitation at both lower and elevated temperatures, e.g. at temperatures of from 5° up to 50° C. In contrast, for compositions formulated with a carrier comprising all three ingredients, no precipitation of the cyclosporin is observed on storage over longer periods of time, both at lower and elevated temperatures, e.g. at temperatures of from 5° to 50° C., even when higher concentrations of cyclosporin, e.g. as aforesaid, are present. The compositions of the invention thus have the advantage of a greatly improved shelf-life with reduced temperature criticality. Unlike compositions in which one of the ingredients (i) and (iii) is omitted, they can be transported and kept in reserve at both lower and elevated temperatures, for periods in excess of several months for later use as, and when, required.

Compositions comprising a three component system (a)+(i)+(iii) also have the advantage of providing a self-emulsifying system in the presence of water, without immediate precipitation of the active ingredient. This is of importance in respect to the bio-availability of the active agent, since precipitation in e.g. the aqueous medium of the stomach or on intra-muscular injection leads to severely impaired resorption. The occurrence of problems in relation to cyclosporin bio-availability employing hitherto known formulations has been recognised and discussed e.g. in Calne et al., "IRCS Medical Science; Drug Metabolism and Toxicology; Immunology and Allergy; Kidneys and Urinary System; Pharmacology; Surgery and Transplantation" 5, 595, (1977).

The properties of the compositions according to the invention may be determined in conventional manner. The stability of solutions particularly against crystallization-out of the active agent may be determined using known tests. Tolerability of injection forms may be determined by observing the extent of bleeding and inflammations after injection, e.g. into thighs of rabbits and rhesus monkeys, and the time taken for these to heal, as well as by using other usual tolerability tests.

The absorption of the pharmacologically active peptide, e.g. rapid onset of a satisfactory concentration of the peptide in the blood, and a high total absorption of the peptide over 24 hours, is indicated in standard tests.

In one test a pharmaceutical composition according to the invention is administered to rabbits, rats, dogs or rhesus monkeys orally, intramuscularly or subcutaneously, at a dose of from 2 to 600 mg/kg animal body weight of active peptide. Blood serum samples and urine samples are taken at regular intervals thereafter, e.g. every hour, and are analysed for the concentration of peptide therein in conventional manner.

For example the pharmacological activity in a sample may be ascertained in conventional manner according to known tests. In the case of cyclosporin A the effect of the peptide present in inhibiting lymphocyte proliferation may be ascertained. Thus the blood serum is collected at regular intervals after administration, and is added at a concentration of from 0.3 to 10% to a mouse in vitro spleen cell suspension in which lymphocyte proliferation is induced by Concavalin A over a 72 hour culture period. $^3$-H-thymidine is then added and the thymidine incorporation after 24 hours is measured to indicate the lymphocyte proliferation.

If desired, the peptide may be administered in radioactive form. For example in the case of the cyclosporins, in one experiment 100 mg of $^3$H-labelled cyclosporin A (prepared by cultivation of the known strain *Tolypocladium inflatum* Gams NRRL 8044 in the presence of methionine marked with tritium in the SCH$_3$ group thereof) contained in a pharmaceutical composition according to the invention in the form of a drinking solution, or in a capsule, is administered perorally, or in the form of an injection solution is administered intramuscularly, to male beagle dogs. Blood samples are obtained from each dog every 15 minutes after administration up to 1 hour after administration and thereafter every hour thereafter up to 8 hours after administration. The urine is collected also. Determination of the ratio-activity in the blood and in the urine indicates the peptide absorption.

The amount of peptide to be administered in the pharmaceutical compositions according to the invention will naturally depend upon the mode of administration, the effect desired and the condition to be treated.

In general the amount of peptide to be administered in a pharmaceutical composition according to invention will be of the same order to that administered by the same route in other pharmaceutical compositions.

In the case of the cyclosporins, the amounts to be administered for a therapeutically effective amount are well-known. When using compositions according to the invention a daily dose of from about 3 mg/kg to about 50 mg/kg is indicated in order to treat chronic inflammations or to provoke an immunosuppressive effect.

The following examples illustrate the invention. All temperatures are in degrees Centigrade.

EXAMPLE 1

Drink Solutions (1a) 200 mg of cyclosporin A are dissolved on stirring in 1 ml of a mixture of Labrafil M 1944 CS and absolute ethanol (parts by weight 40:15) at 25°. 0.4 ml of olive oil or corn oil are added. The resultant mixture is filtered and filled into a small vial. The final solution contains for every 10 parts by weight of Labrafil; ca. 3 parts by weight of cyclosporin A, 3 parts by weight of ethanol and 5 parts by weight of olive oil or corn oil.

(1b) The composition of example (1a) may be produced on a large scale as follows:

150.00 kg Labrafil M 1944 CS are stirred for 5 minutes with 50.00 kg absolute ethanol. 50.00 kg cyclosporin A are then added to the mixture with stirring over a period of ca. 40 minutes until the cyclosporin A is completely dissolved. Ca. 212.00 kg olive oil are then added with stirring for ca. 10 minutes to give a total end weight of 462.50 kg. The obtained solution is filtered and filled into 50 ml containers which are then sealed, to give a total volume per container of 51.5 ml. As with any liquid composition comprising olive oil as an ingredient, the means of filtration employed is important.

If filtration is insufficient, and impurities, such as higher fatty acid ester components, present in the olive oil are not fully removed, these will separate out in the course of 1 to 2 months, producing a light ground sediment. While this is not critical to utility and does not reflect on the stability of the composition, i.e. on the stability of the active ingredient in the solution, for commercial purposes such sedimentation is preferably to be avoided. Suitably filtration for examples 1a and 1b is carried out by pre-filtration using a Seitz Supra 1000 (cellulose-Kieselguhr) layer filter or a Millipore Lifeguard CP 20 (fiber flass) filter, followed by filtration through a 7 μm polypropylene filtration cartridge, e.g. such as a Pall HDC BE cartridge.

For the purposes of administration composition 1a or 1b is advantageously mixed with a chocolate flavouring agent, e.g. as follows:

15 g Caotina (a chocolate flavouring agent available from the company Wander) are stirred into 50 ml of milk and the desired dosage of cyclosporin A drink-solution (7–12 ml of composition 1c) are added. The mixture is ingested immediately.

(1c) The following composition is obtained analogously to example (1a):

|   | Component | Content | |
|---|---|---|---|
| (a) | Cyclosporin A | 100.00 mg | |
|   | Labrafil M 1944 CS | 300.00 mg | |
| (i) | 100% Ethanol | 100.00 mg | |
| (iii) | Olive oil | ca. 425.00 mg | to give an end volume of 1.00 ml. |

The compositions 1a–1c above exhibit the advantages of a combination of carriers (a), (i) and (iii) as hereinbefore described.

EXAMPLE 2

Parenteral Forms for I.M. and S.C. Administration 100 mg of cyclosporin A are dissolved on stirring in a mixture of 40 mg ethanol and 0.5 ml Miglyol 812 at 25° C. The mixture is finally made up to 1 ml with Miglyol 812 and filled under sterile conditions into an ampoule. The final solution contains for every 10 parts by weight of Miglyol 812, 1 part by weight of cyclosporin A.

EXAMPLE 3

Parenteral Forms for I.M. and S.C. Administration 100 mg of cyclosporin A are dissolved on stirring in a mixture of 40 mg ethanol, 100 mg Labrafil M 1944 CS and 200 mg Miglyol 812 at 25°. The resulting mixture is made up to 1 ml with olive oil and filled under sterile conditions into an ampoule.

The final solution contains for every 10 parts by weight of Miglyol 812, 5 parts by weight each of cyclosporin A and Labrafil and 25 parts by weight of olive oil.

EXAMPLE 4

Parenteral Form for I.M. and S.C. Administration 200 mg of cyclosporin A are dissolved in a mixture of 400 mg benzoic acid benzyl ester and 0.3 ml Miglyol 812 at 25°. The resultant mixture is made up to 1 ml with Miglyol 812 and filled under sterile conditions into an ampoule.

The final solution contains for every 10 parts by weight of Miglyol 812, 6 parts by weight of cyclosporin A.

EXAMPLE 5

Parenteral Form for I.M. and S.C. Administration 200 mg of cyclosporin A are dissolved on stirring in a mixture of 50 mg ethanol, 300 mg Labrafil M 1944 CS and 0.3 ml Miglyol 812 at 25°. The resultant solution is made up to 1 ml with Miglyol 812 and filled under sterile conditions into an ampoule.

The final solution contains for every 10 parts by weight of Miglyol 812, 7 parts by weight of Labrafil and 5 parts by weight of cyclosporin A.

EXAMPLE 6

Capsules for Oral Administration 200 mg of cyclosporin A are dissolved on stirring in a mixture of 600 mg Glycerol mono-oleate and 30 mg ethanol at 30°. The final solution is encapsulated in a soft gelatine capsule.

What we claim is:

1. A liquid pharmaceutical composition comprising a pharmaceutically effective amount of a cyclosporin and a carrier comprising the following components:
   (a) a trans-esterification product of a natural vegetable oil triglyceride and a polyalkylene polyol;
   (b) a vegetable oil; and
   (c) ethanol; whrein the ratio of component (a) to cyclosporin is 10:0.2 to 10 parts by weight; the amount of component (b) is 35 to 60% by weight based on the total weight of the composition, and the amount of component (c) is 1 to 20% by weight based on the total weight of the composition.

2. Composition according to claim 1, wherein the cyclosporin is cyclosporin A.

3. Composition according to claim 1, wherein the cyclosporin is dihydrocyclosporin C.

4. Composition according to claim 1, wherein the cyclosporin is cyclosporin D.

5. Composition according to claim 1, wherein the cyclosporin is dihydrocyclosporin D.

6. Composition according to claim 1, wherein component (a) is a trans-esterification product of two molar parts of a natural vegetable oil triglyceride and one molar part of a polyethylene glycol of MW 200 to 800.

7. Composition according to claim 6, wherein the natural vegetable oil is kernel oil.

8. Composition according to claim 7, wherein component (a) is a polyoxyethylated kernel oil mixture, having a density of $D^{20}=0.940-0.965$, an acid number $<2$, an iodine number$=60-90$, a saponification number$=1-45-175$ and a hydrophilic-lipophilic balance (H.L.B.)$=4$.

9. Composition according to claim 1, wherein component (b) is olive oil or corn oil.

10. Composition according to claim 9, wherein component (b) is olive oil.

11. Composition according to claim 1, wherein the ratio of component (a) to cyclosporin is 10:1 to 10 parts by weight.

12. Composition according to claim 11, wherein the ratio is 10:1 to 7 parts by weight.

13. Composition according to claim 1, wherein components (b) and (c) together are present in an amount of up to 60% by weight based on the total weight of the composition.

14. Composition according to claim 1, formulated as solution for oral administration.

15. A liquid pharmaceutical composition comprising a pharmaceutically effective amount of a cyclosporin and a carrier comprising the following components:
   (a) a trans-esterification product of a hydrogenated vegetable oil triglyceride and a polyalkylene polyol;
   (b) a vegetable oil; and
   (c) ethanol;
wherein the ratio of component (a) to cyclosporin is 10:0.2 to 10 parts by weight; the amount of component (b) is 35 to 60% by weight based on the total weight of the composition, and the amount of component (c) is 1 to 20% by weight based on the total weight of the composition.

* * * * *